United States Patent
Pandev

(10) Patent No.: US 10,152,654 B2
(45) Date of Patent: Dec. 11, 2018

(54) SIGNAL RESPONSE METROLOGY FOR IMAGE BASED OVERLAY MEASUREMENTS

(71) Applicant: KLA-Tencor Corporation, Milpitas, CA (US)

(72) Inventor: Stilian Ivanov Pandev, Santa Clara, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/624,485

(22) Filed: Feb. 17, 2015

(65) Prior Publication Data

US 2015/0235108 A1    Aug. 20, 2015

Related U.S. Application Data

(60) Provisional application No. 61/942,204, filed on Feb. 20, 2014.

(51) Int. Cl.
*G06K 9/62* (2006.01)
*G06K 9/46* (2006.01)
(Continued)

(52) U.S. Cl.
CPC ....... *G06K 9/6255* (2013.01); *G01N 21/9501* (2013.01); *G06T 7/0004* (2013.01);
(Continued)

(58) Field of Classification Search
CPC ......... G06T 2207/30148; G06T 7/0006; G06T 2207/20076; G06T 7/0008;
(Continued)

(56) References Cited

U.S. PATENT DOCUMENTS 6,023,338 A    2/2000  Bareket
6,563,324 B1   5/2003  Nichani
(Continued)

OTHER PUBLICATIONS

International Search Report dated May 29, 2015, for PCT Application No. PCT/US2015/016841 filed on Feb. 20, 2015 by KLA-Tencor Corporation, 3 pages.

*Primary Examiner* — Kim Vu
*Assistant Examiner* — Michael Vanchy, Jr.
(74) *Attorney, Agent, or Firm* — Spano Law Group; Joseph S. Spano

(57) ABSTRACT

Methods and systems for creating an image-based measurement model based only on measured, image-based training data are presented. The trained, image-based measurement model is then used to calculate values of one or more parameters of interest directly from measured image data collected from other wafers. The image-based measurement models receive image data directly as input and provide values of parameters of interest as output. In some embodiments, the image-based measurement model enables the direct measurement of overlay error. In some embodiments, overlay error is determined from images of on-device structures. In some other embodiments, overlay error is determined from images of specialized target structures. In some embodiments, image data from multiple targets, image data collected by multiple metrologies, or both, is used for model building, training, and measurement. In some embodiments, an optimization algorithm automates the image-based measurement model building and training process.

24 Claims, 10 Drawing Sheets

(51) Int. Cl.
*G06K 9/66* (2006.01)
*G06T 7/00* (2017.01)
*G01N 21/95* (2006.01)

(52) U.S. Cl.
CPC ............ *G06K 2209/19* (2013.01); *G06T 2207/20081* (2013.01); *G06T 2207/30148* (2013.01)

(58) Field of Classification Search
CPC ......... G06T 2207/20081; G06T 7/0004; G06T 7/0028; G06T 7/001; G06T 2207/10056; G06T 2207/10061; G06T 2207/20084; G06T 7/33; G06F 17/5045; G06F 17/5081; G01N 21/9501; G01N 21/956; G01N 23/225; G03F 1/84; G03F 7/70633; G03F 7/70625; G03F 7/70641; G06K 9/6255; G06K 9/6247; G06K 9/2018; G06K 9/4604; G06K 9/6256; G06K 9/629; G06K 2209/19; G06K 9/522; G06K 9/624; G06K 9/6269; G06K 9/6282; G01B 11/02; G01B 11/272; G01B 2210/56; H04N 5/2256; H04N 17/002; G01Q 60/24; H01J 2237/24592; H01J 2237/2816; H01J 2237/2817; H01J 37/28

See application file for complete search history.

(56) References Cited

U.S. PATENT DOCUMENTS

| | | |
|---|---|---|
| 6,716,646 B1 | 4/2004 | Wright et al. |
| 6,778,275 B2 | 8/2004 | Bowes |
| 6,787,773 B1 | 9/2004 | Lee |
| 6,992,764 B1 | 1/2006 | Yang et al. |
| 7,321,426 B1 | 1/2008 | Poslavsky et al. |
| 7,626,702 B2 | 12/2009 | Ausschnitt et al. |
| 7,842,933 B2 | 11/2010 | Shur et al. |
| 7,873,585 B2 | 1/2011 | Izikson |
| 8,068,662 B2 | 11/2011 | Zhang et al. |
| 8,138,498 B2 | 3/2012 | Ghinovker |
| 2003/0021465 A1 | 1/2003 | Adel et al. |
| 2004/0018653 A1 | 1/2004 | Johnson et al. |
| 2004/0267397 A1* | 12/2004 | Doddi .................. G01B 11/24 700/110 |
| 2007/0221842 A1 | 9/2007 | Morokuma et al. |
| 2008/0281545 A1* | 11/2008 | McIntyre ........... G01R 31/2894 702/119 |
| 2009/0063378 A1* | 3/2009 | Izikson ................ G05B 13/027 706/21 |
| 2009/0152463 A1 | 6/2009 | Toyoda et al. |
| 2010/0281981 A1* | 11/2010 | Tas ..................... G01N 21/1717 73/570 |
| 2011/0266440 A1 | 11/2011 | Boughorbel et al. |
| 2012/0094400 A1 | 4/2012 | Adel et al. |
| 2012/0292502 A1 | 11/2012 | Langer et al. |
| 2013/0208279 A1 | 8/2013 | Smith |
| 2013/0305206 A1 | 11/2013 | Pandev |

\* cited by examiner

SIGNAL RESPONSE METROLOGY FOR IMAGE BASED OVERLAY MEASUREMENTS

CROSS REFERENCE TO RELATED APPLICATION

The present application for patent claims priority under 35 U.S.C. § 119 from U.S. provisional patent application Ser. No. 61/942,204, entitled "Signal Response Metrology For On-Device Image Based Overlay Measurements," filed Feb. 20, 2014, the subject matter of which is incorporated herein by reference in its entirety.

TECHNICAL FIELD

The described embodiments relate to metrology systems and methods, and more particularly to methods and systems for improved image based measurements.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Overlay error refers to the relative position of structures on different layers of a wafer. The greater the overlay error, the more the structures are misaligned. If the overlay error is too great, the performance of the manufactured electronic device may be compromised.

Overlay error is typically evaluated based on measurements of specialized target structures formed at various locations on the wafer by a lithography tool. The target structures may take many forms, such as a box in box structure. In this form, a box is created on one layer of the wafer and a second, smaller box is created on another layer. The localized overlay error is measured by comparing the alignment between the centers of the two boxes. Such measurements are taken at locations on the wafer where target structures are available.

Image based overlay error measurement typically involves the analysis of images of the specialized target structures to estimate overlay error. Typically, the image analysis involves the recognition of specific target features (e.g., line segments, boxes, etc.) in the image and overlay error is calculated based on relative locations of these features. Typically, the specialized target structures are specific to the image processing algorithm. For example, the line segments associated with the overlay target (e.g., box-in-box target, frame-in-frame target, advanced imaging metrology (AIM) target) are specifically designed to comply with the specifics of the algorithm. For this reason, traditional image based overlay metrology analysis algorithms cannot perform reliably with arbitrary overlay targets or device structures.

In addition, some information is lost because the algorithms work only on specific areas of the image. In other words, the selection of particular line edges, etc. as the focal point for evaluating overlay error ignores contributions that might be made by other pixels in the image.

Moreover, traditional image based algorithms are sensitive to process variations, asymmetry, and optical system errors as these algorithms lack a systematic way to capture the impact of these error sources on the captured images.

Future overlay metrology applications present challenges for metrology due to increasingly small resolution requirements and the increasingly high value of wafer area. Thus, methods and systems for improved overlay measurements are desired.

SUMMARY

Methods and systems for creating an image-based measurement model based only on measured, image-based training data (e.g., images collected from a Design of Experiments (DOE) wafer) are presented. The trained, image-based measurement model is then used to calculate values of one or more parameters of interest directly from measured image data collected from other wafers.

In one aspect, the trained, image-based measurement models described herein receive image data directly as input and provide values of one or more parameters of interest as output. By streamlining the measurement process, the predictive results are improved along with a reduction in computation and user time.

In another aspect, values of parameters of interest may be determined from images of on-device structures. In some embodiments, images of on-device structures are used to train an image-based measurement model as described herein. The trained, image-based measurement model is then used to calculate values of one or more parameters of interest directly from images of the same on-device structures collected from other wafers.

By using only raw image data to create the image-based measurement model, as described herein, the errors and approximations associated with traditional image based metrology methods are reduced. In addition, the image-based measurement model is not sensitive to systematic errors, asymmetries, etc. because the image-based measurement model is trained based on image data collected from a particular metrology system and used to perform measurements based on images collected from the same metrology system.

In a further aspect, overlay error between structures formed on a substrate by successive lithographic processes is directly measured based on an image-based measurement model created from raw image data as described herein. The image-based measurement model is trained based on set of images with known overlay variations. The trained image-based measurement model then is used to predict the overlay errors from an unknown image. In general, the structures may be located on the same layer or on different layers of the substrate.

In another further aspect, the methods and systems described herein are not limited only to the measurement of overlay errors. In general, the aforementioned image-based measurement techniques may be applied to the measurement of other process, structure, dispersion parameters, or any combination of these parameters. By way of non-limiting example, any of critical dimension, overlay error, focus, and dose may be measured using the techniques described herein.

In another further aspect, the methods and systems for training the image-based measurement model include an optimization algorithm to automate any or all of the elements required to arrive at a trained image-based measurement model.

In a further aspect, image data from multiple targets having different structure, but formed by the same process conditions is collected for model building, training, and measurement. This increases the information embedded in the model and reduces the overlay correlation to process or other parameter variations.

In another further aspect, image data derived from measurements performed by a combination of multiple, different measurement techniques is collected for model building, training, and measurement. The use of measurement data associated with multiple, different measurement techniques increases the information content in the combined set of signals and reduces the overlay correlation to process or other parameters variations.

In yet another aspect, the image-based measurement model results described herein can be used to provide active feedback to a process tool (e.g., lithography tool, etch tool, deposition tool, etc.).

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
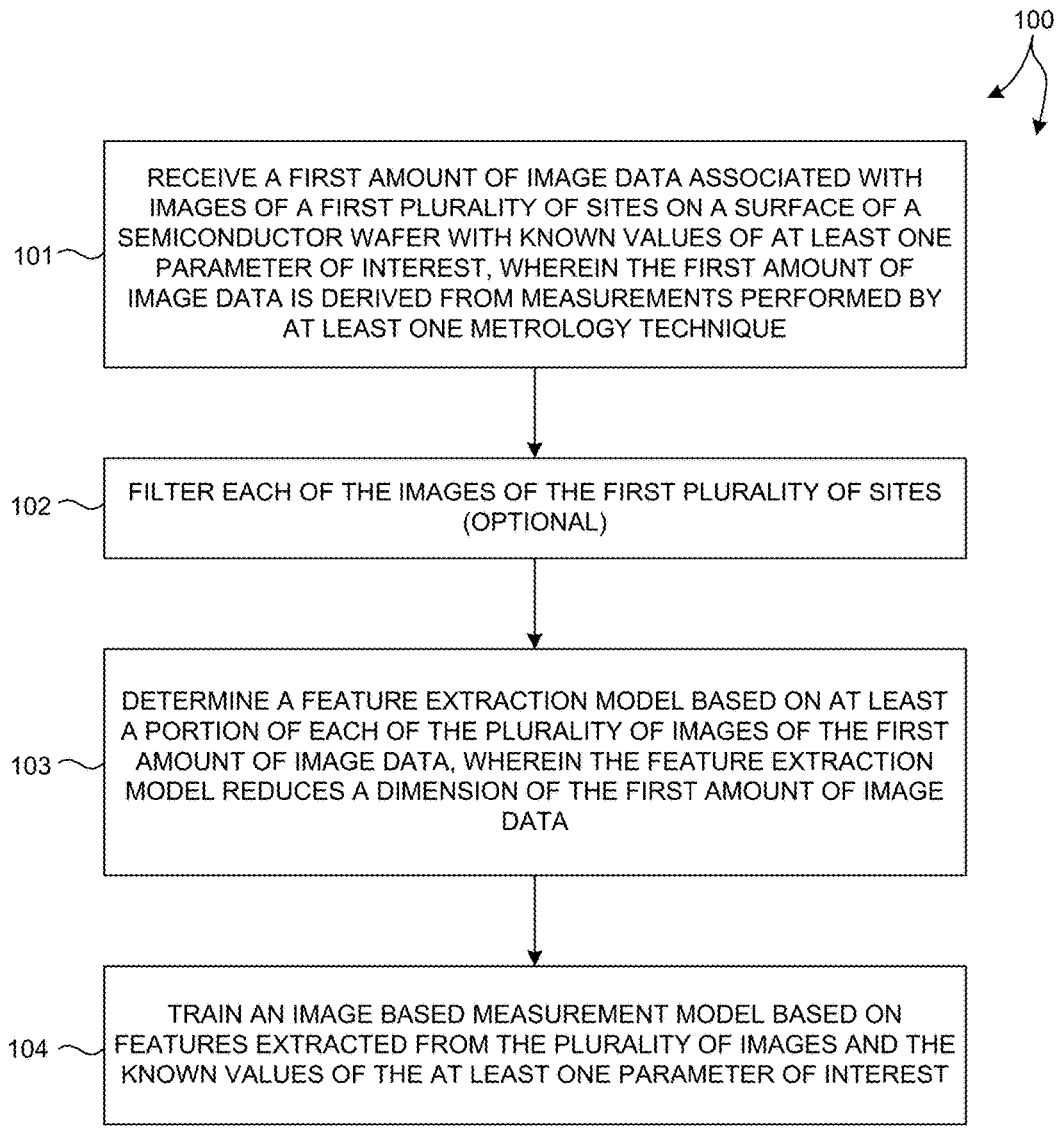
FIG. 1 is a flowchart illustrative of a method 100 of training an image-based measurement model as described herein.

Reference will now be made in detail to background examples and some embodiments of the invention, examples of which are illustrated in the accompanying drawings.

Methods and systems for creating an image-based measurement model based only on measured, image-based training data (e.g., images collected from a Design of Experiments (DOE) wafer) are presented. The trained, image-based measurement model is then used to calculate values of one or more parameters of interest directly from measured image data collected from other wafers.

In one aspect, the trained, image-based measurement models described herein receive image data directly as input and provide values of one or more parameters of interest as output. By streamlining the measurement process, the predictive results are improved along with a reduction in computation and user time.

In another aspect, values of parameters of interest may be determined from images of on-device structures. In some embodiments, images of on-device structures are used to train an image-based measurement model as described herein. The trained, image-based measurement model is then used to calculate values of one or more parameters of interest directly from images of the same on-device structures collected from other wafers. In these embodiments, the use of specialized targets is avoided. In one example, overlay measurements are performed using in-die device structures as an overlay metrology target. This enables in-die measurements and avoids the complexity of using specialized overlay metrology targets and tuning image analysis algorithms to these specialized targets. In some examples, the image-based measurement model can be created in less than an hour. In addition, by employing a simplified model, measurement time is reduced compared to existing image based metrology methods.

By using only raw image data to create the image-based measurement model, as described herein, the errors and approximations associated with traditional image based metrology methods are reduced. In addition, the image-based measurement model is not sensitive to systematic errors, asymmetries, etc. because the image-based measurement model is trained based on image data collected from a particular metrology system and used to perform measurements based on images collected from the same metrology system.

In a further aspect, overlay error between structures formed on a substrate by successive lithographic processes is directly measured based on an image-based measurement model created from raw image data as described herein. The image-based measurement model is trained based on set of images with known overlay variations. The image-based measurement model then is used to predict the overlay errors from an unknown image. In general, the structures may be located on the same layer or on different layers of the substrate.

In general, the methods and systems described herein analyze the image as a whole. Instead of recognizing individual features in the image, each pixel is considered as an individual signal containing information about (or sensitive to) overlay errors, and other parameters (e.g., structural parameters, process parameters, dispersion parameters, etc.).

Figure 19:
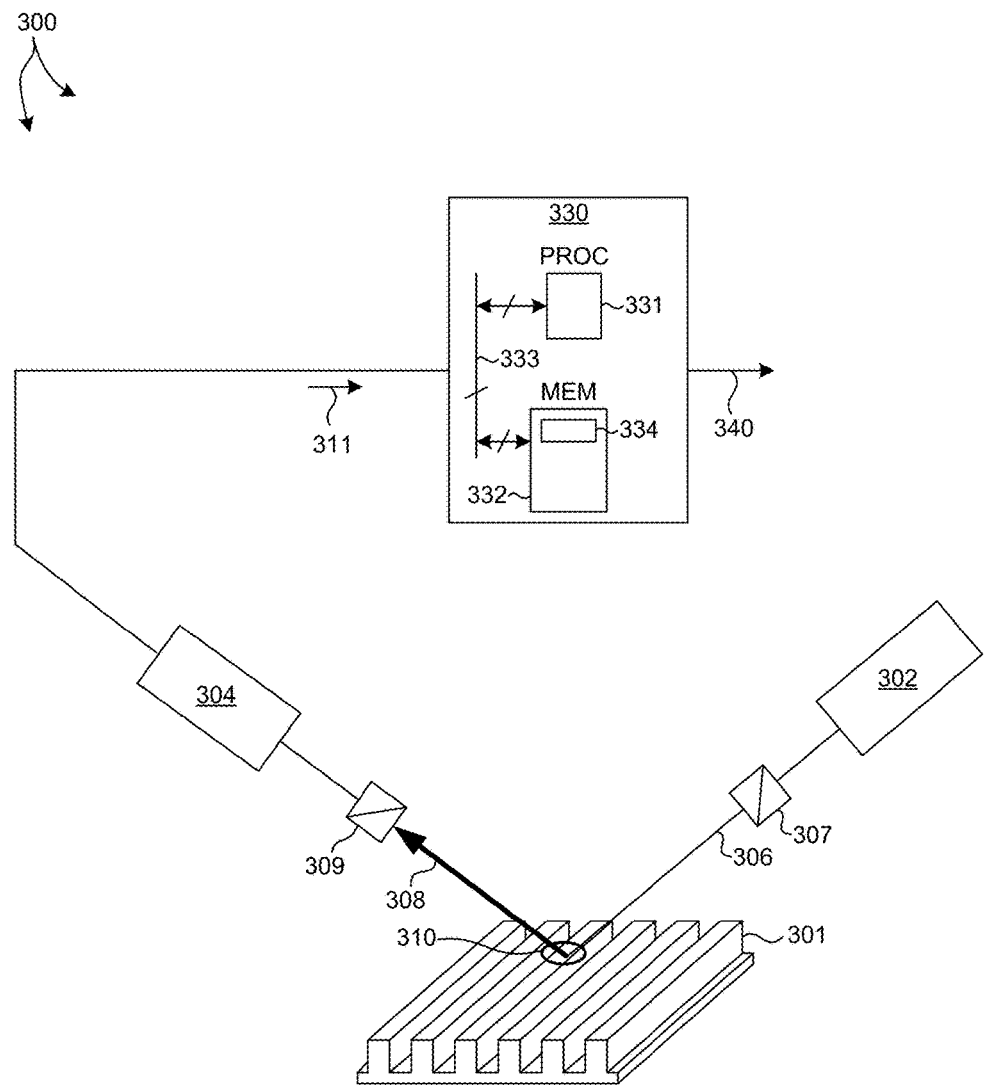
FIG. 19 illustrates a system 300 for estimating parameters of interest from images collected from a specimen in accordance with the exemplary methods presented herein.

FIG. 1 illustrates a method 100 suitable for implementation by a metrology system such as metrology system 300 illustrated in FIG. 19 of the present invention. In one aspect, it is recognized that data processing blocks of method 100 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 101, a first amount of image data associated with images of a first plurality of sites on a surface of a semiconductor wafer is received by a computing system (e.g., computing system 330). The images exhibit known variations of at least one parameter of interest. The image data is derived from measurements performed by at least one metrology technique. The images can be obtained from an optical imaging system, a scanning electron microscope, or other image forming systems.

Figure 18:
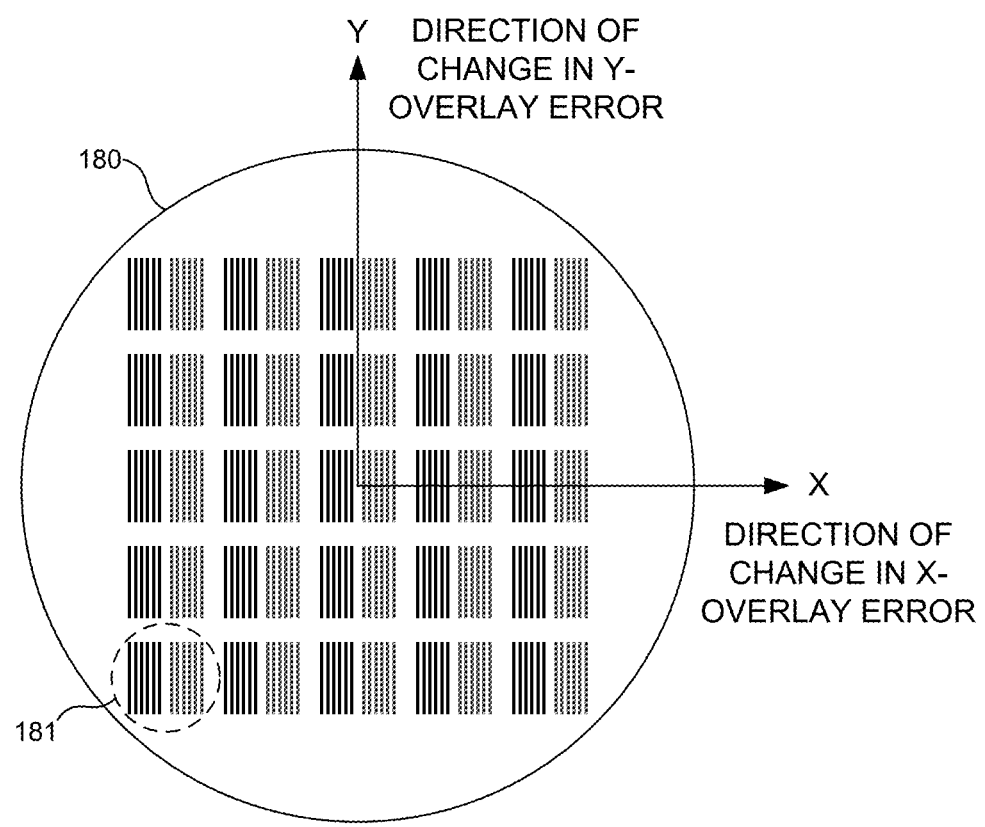
FIG. 18 depicts a DOE wafer 180 having a grid of targets that exhibit known variations in overlay error in one embodiment.

In some embodiments, variations of the parameter(s) of interest are organized in a Design of Experiments (DOE) pattern on the surface of a semiconductor wafer (e.g., DOE wafer). In this manner, the measurement sites interrogate different locations on the wafer surface that correspond with different values of the parameter(s) of interest. In one example, the DOE pattern is an overlay error pattern. Typically, a DOE wafer exhibiting an overlay error pattern includes a grid pattern of measurement sites. In one grid direction (e.g., the x-direction), the overlay is varied in the x-direction while the overlay in the y-direction is held constant. In the orthogonal grid direction (e.g., the y-direction), the overlay error in the y-direction is varied while the overlay error in the x-direction is held constant. In this manner, image data collected from the DOE wafer includes data associated with known variations in the overlay in both the x and y directions. FIG. 18 depicts a DOE wafer 180 having a grid of targets (e.g., target 181) that exhibit known variations in overlay error. The x-direction overlay errors vary as a function of location on the DOE wafer 180 in the x-direction. The y-direction overlay errors vary as a function of location on the DOE wafer 180 in the y-direction. In some examples, the x and y overlay errors range from −20 nanometers to 20 nanometers. In some other examples, the x and y overlay errors range from −80 to 80 nanometers.

In the aforementioned example, the image data is associated with a DOE wafer processed with known variations in overlay error. However, in general, image data associated with any known variation of process parameters, structural parameter, dispersion, etc., may be contemplated. The images of the DOE wafer should exhibit ranges of the parameter(s) of interest (e.g., overlay error) and should also exhibit ranges of other noise sources such as process variations (e.g., focus/dose) and optical system errors (e.g., camera offset).

Figure 3:
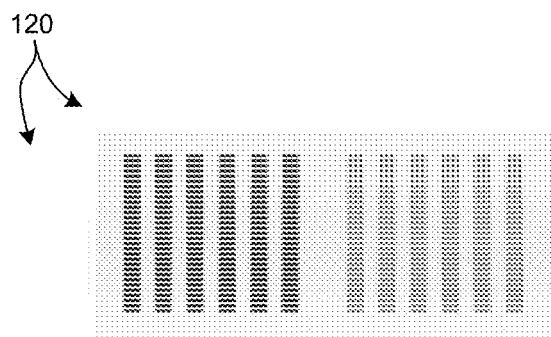
FIG. 3 depicts a simulated image 120 of two gratings, each disposed on a different layer of a semiconductor wafer.

FIG. 3 depicts a simulated image 120 of two gratings, each disposed on a different layer of a semiconductor wafer. In this simulation, the grating pitch is one micron. The width of each line of the grating (i.e., critical dimension of the grating) is five hundred nanometers. The range of overlay error is sixteen nanometers in both the x and y directions over three hundred different images. To introduce additional errors into the analysis, the width of each line of the grating is varied by five nanometers over the three hundred images, and the camera offset error (i.e., whole image shift) is varied by four pixels in both the x and y directions over the three hundred images. In this simulation, the pixel resolution is one pixel every ten nanometers.

Figure 9:
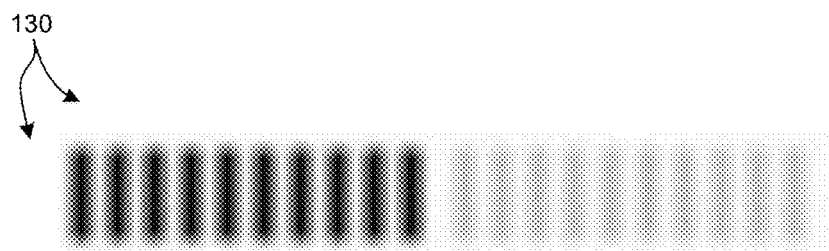
FIG. 9 depicts a simulated image 130 of two gratings, each disposed on a different layer of a semiconductor wafer in another embodiment.

FIG. 9 depicts a simulated image 130 of two gratings, each disposed on a different layer of a semiconductor wafer. In this simulation, the grating pitch is four hundred nanometers. The width of each line of the grating (i.e., critical dimension of the grating) is two hundred nanometers. The range of overlay error is one hundred nanometers in both the x and y directions over two hundred different images. To introduce additional errors into the analysis, the width of each line of the grating is varied by five nanometers over the two hundred images, and the camera offset error (i.e., whole image shift) is varied by five pixels in both the x and y directions over the two hundred images. In this simulation, the pixel resolution is one pixel every ten nanometers.

In optional block 102, each of the images received in block 101 is filtered by one or more image filters. Image filters may be employed to for noise reduction, contrast enhancement, etc. The image filters employed may be selected by a user or by an automatic procedure. The number of different image filters and the parameters associated with each selected filter are chosen to improve the final measurement result without undue computational burden. Although, the use of image based filters may be advantageous, in general, it is not necessary. In this sense, block 102 is optional.

In block 103, a feature extraction model is determined based on at least a portion of each of the plurality of images of the first amount of image data. The feature extraction model reduces a dimension of the first amount of image data. A feature extraction model maps the original signals to a new reduced set of signals. The transformation is determined based on the variations in the parameter(s) of interest in the first amount of image data. Each pixel of each image is treated as an original signal that changes within the process range for different images in the first amount of image data. The feature extraction model may be applied to all of the image pixels, or a subset of image pixels. In some examples, the pixels subject to analysis by the feature extraction model are chosen randomly. In some other examples, the pixels subject to analysis by the feature extraction model are chosen due to their relatively high sensitivity to changes in the parameter(s) of interest. For example, pixels that are not sensitive to changes in the parameter(s) of interest may be ignored. In the examples depicted in FIGS. 3 and 9, five thousand pixels were sampled randomly for analysis.

By way of non-limiting example, the feature extraction model may a principal component analysis (PCA) model, a kernel PCA model, a non-linear PCA model, an independent component analysis (ICA) model or other dimensionality reduction methods using dictionaries, a discrete cosine transform (DCT) model, fast fourier transform (FFT) model, a wavelet model, etc.

One or more features are extracted from the first amount of image data. In some examples, the image data is analyzed using Principal Components Analysis (PCA), or non-linear PCA, to extract features that most strongly reflect the variations in the parameter(s) of interest that are present at the different measurement sites. In some other examples, a signal filtering technique may be applied to extract signal data that most strongly reflects the parameter variations present at the different measurement sites. In some other examples, individual signals that most strongly reflect the parameter variations present at the different measurement sites may be selected from multiple signals present in the image data.

Figure 4:
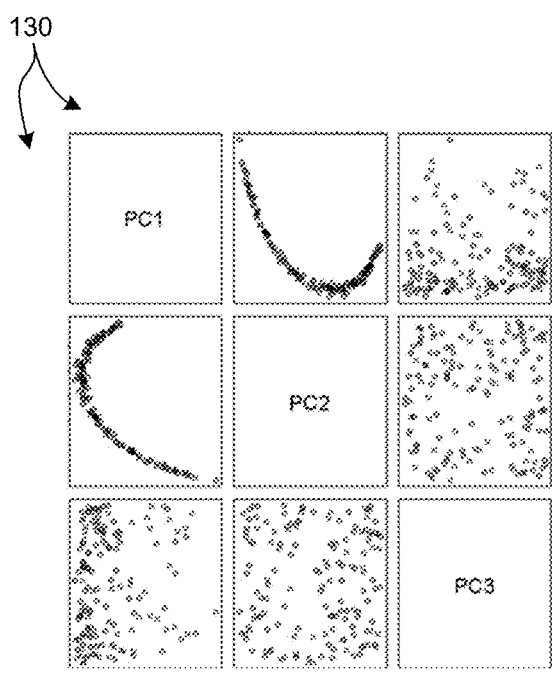
FIG. 4 illustrates a matrix 130 of principal components maps of images collected from a DOE wafer that includes known variations in overlay error.

FIG. 4 illustrates a matrix 130 of principal components maps of images collected from a DOE wafer that includes known variations in overlay error. As illustrated, the first and second principal components are strongly correlated. This indicates the presence of systematic behavior across the image data set and that the first and second principal components are responsive to overlay error. FIG. 4 also illustrates that the third principal component is weakly correlated with the first two principal components. This indicates that the third principal component is more responsive to noise or other unwanted perturbations than the first two principal components. In this example, it is preferred to utilize only the first two principal components to train the image based measurement model. In this manner, principal components that primarily reflect noise are truncated for purposes of model building, and subsequent image-based measurement analysis.

In block 104, an image based measurement model is trained based on features extracted from the plurality of images and the known values of the at least one parameter of interest. The image-based measurement model is structured to receive image data generated by a metrology system at one or more measurement sites, and directly determine the parameter(s) of interest associated with each measurement target. In some embodiments, the image-based measurement model is implemented as a neural network model. In one example, the number of nodes of the neural network is selected based on the features extracted from the image data. In other examples, the image-based measurement model may be implemented as a linear model, a polynomial model, a response surface model, a support vector machines model, or other types of models. In some examples, the image-based measurement model may be implemented as a combination of models. The selected model is trained based on the reduced set of signals determined from the feature extraction model and the known variations in the parameter(s) of interest. The model is trained such that its output fits the defined variations in the parameter(s) of interest for all the images in the parameter variation space defined by the DOE images.

Figure 2:
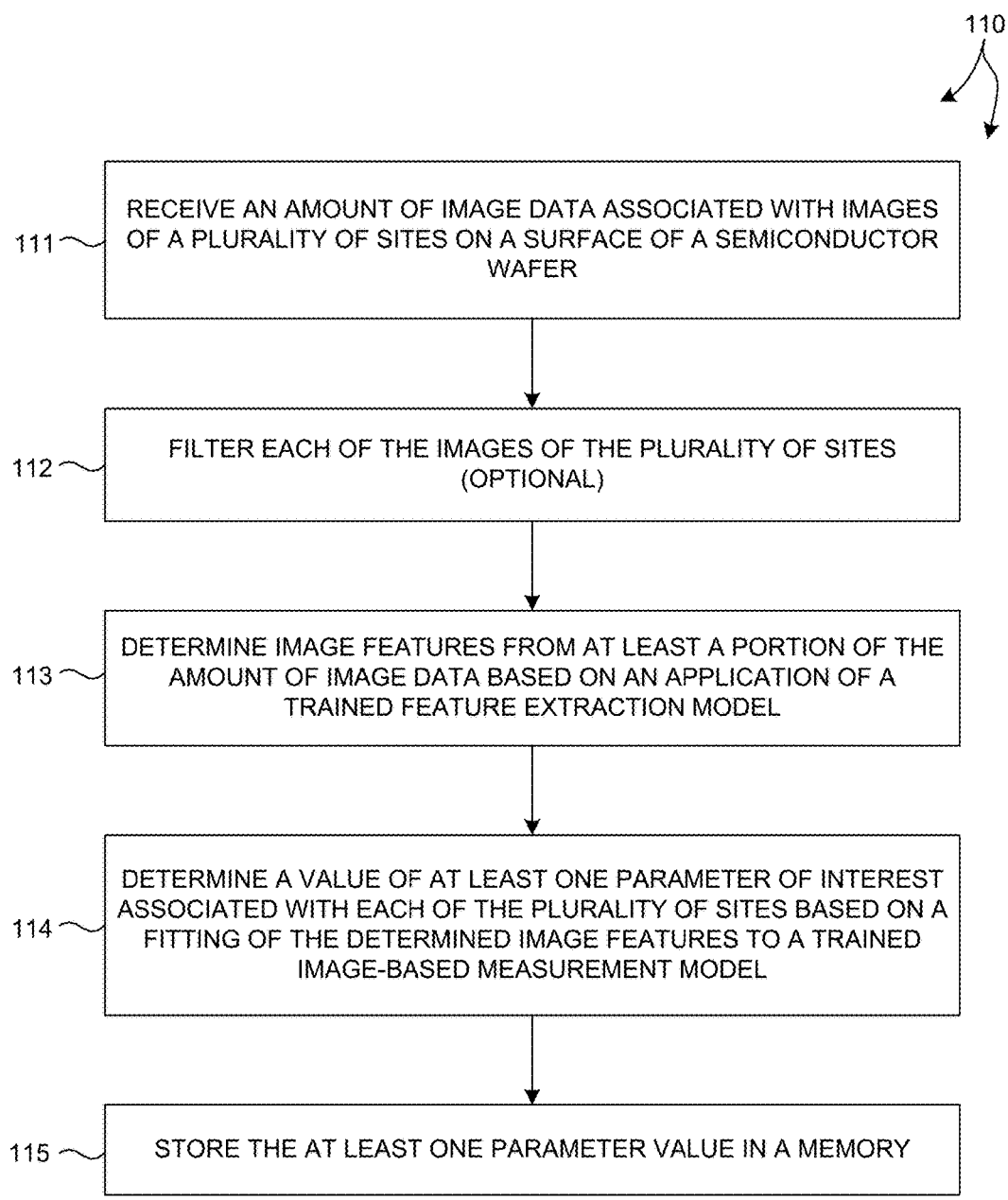
FIG. 2 is a flowchart illustrative of a method 110 of measuring a parameter of interest using a trained, image-based measurement model generated by method 100.

In another aspect, the trained model is employed as the measurement model for measurement of other wafers. FIG. 2 illustrates a method 110 suitable for implementation by a metrology system such as metrology system 300 illustrated in FIG. 19 of the present invention. In one aspect, it is recognized that data processing blocks of method 110 may be carried out via a pre-programmed algorithm executed by one or more processors of computing system 330, or any other general purpose computing system. It is recognized herein that the particular structural aspects of metrology system 300 do not represent limitations and should be interpreted as illustrative only.

In block 111, an amount of image data associated with images of a plurality of sites on a surface of a semiconductor wafer is received by a computing system (e.g., computing system 330). The image data is derived from measurements performed by the same metrology technique, or combination of metrology techniques as described with reference to method 100. Similarly, the image data includes images of the same types of structures as described with reference to method 100, but with unknown overlay errors.

In optional block 112, the each of the images received in block 111 is filtered by the same image filter, or combination of image filters as described with reference to method 100. Although, the use of image based filters may be advantageous, in general, it is not necessary. In this sense, block 112 is optional.

In block 113, image features from at least a portion of the amount of image data are determined based on an application of a trained feature extraction model (e.g., the trained feature extraction model described with reference to method 100). It is preferred to extract features from the image data using the same analysis employed to extract features from the training data in method 100. In this manner, the dimension reduction of the acquired image data is performed by the same feature extraction model used to reduce the dimension of the training data.

In block 114, the value of at least one parameter of interest associated with each of the plurality of sites is determined based on a fitting of the determined image features to a trained image-based measurement model (e.g., the trained image-based measurement model described with reference to method 100). In this manner, the parameter(s) of interest are determined based on the trained image-based measurement model and the reduced set of image signals.

In block 115, the determined value(s) of the parameter(s) of interest are stored in a memory. For example, the parameter values may be stored on-board the measurement system 300, for example, in memory 332, or may be communicated (e.g., via output signal 340) to an external memory device.

In some examples, the measurement performance of the trained image-based measurement model is determined by using the model to measure a set of images that have not participated as part of the training data set, but have known overlay error. The differences between the expected and measured overlay are indicative of model performance.

Figure 5:
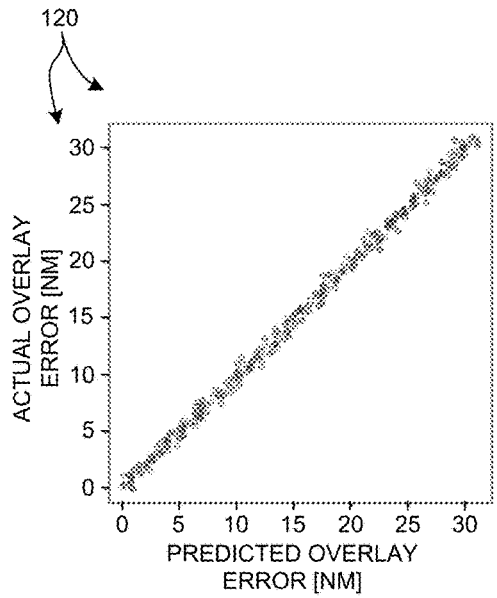
FIG. 5 depicts a plot 120 of simulation results indicative of actual overlay error on the y-axis and corresponding predicted overlay error on the x-axis for the simulation as described with reference to FIG. 3.

FIG. 5 depicts a plot 120 of simulation results indicative of actual overlay error on the y-axis (i.e., known overlay error values) and corresponding predicted overlay error on the x-axis (i.e., as measured by a trained image-based measurement model) for the simulation as described with reference to FIG. 3. The results depicted in plot 120 include measurements of images that participated in the training set and images that did not participate in the training set. As depicted in FIG. 5, the simulated measurement results are tightly grouped with the corresponding, known values.

Figure 6:
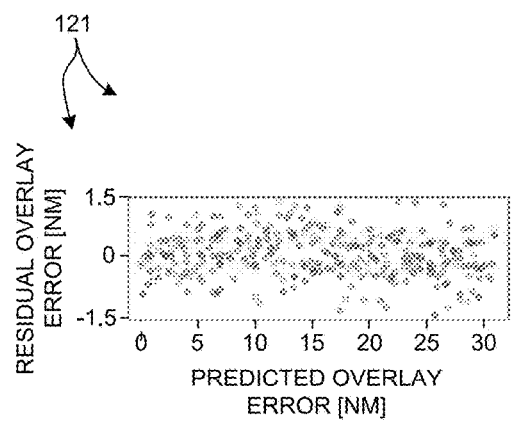
FIG. 6 depicts a plot 121 indicative of the residual overlay error values associated with each measurement point depicted in FIG. 5.

FIG. 6 depicts a plot 121 indicative of the residual overlay error values associated with each measurement point depicted in FIG. 5. The residual overlay value is the difference between the actual overlay error value and the predicted overlay error value.

Figure 7:
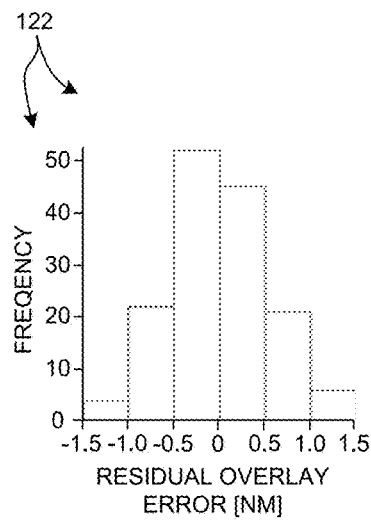
FIG. 7 depicts a plot 122 illustrating the distribution of the residual values depicted in FIG. 6 for measurement points associated with training images.

FIG. 7 depicts a plot 122 illustrating the distribution of the residual values depicted in FIG. 6 for the measurement points associated with training images. The sigma value of the residual value for this set of images is 0.54 nanometers.

Figure 8:
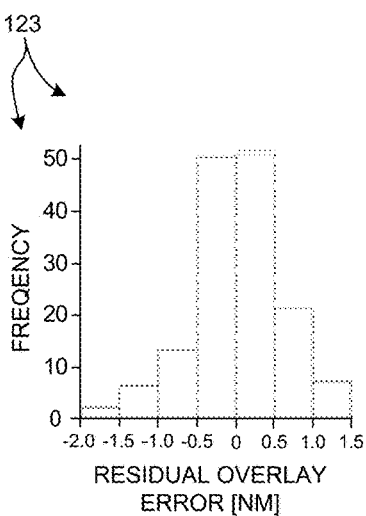
FIG. 8 depicts a plot 123 illustrating the distribution of the residual values depicted in FIG. 6 for measurement points associated with images that did not participate in the training data set.

FIG. 8 depicts a plot 123 illustrating the distribution of the residual values depicted in FIG. 6 for the measurement points associated with images that did not participate in the training data set. The sigma value of the residual value for this set of images is 0.57 nanometers.

Figure 10:
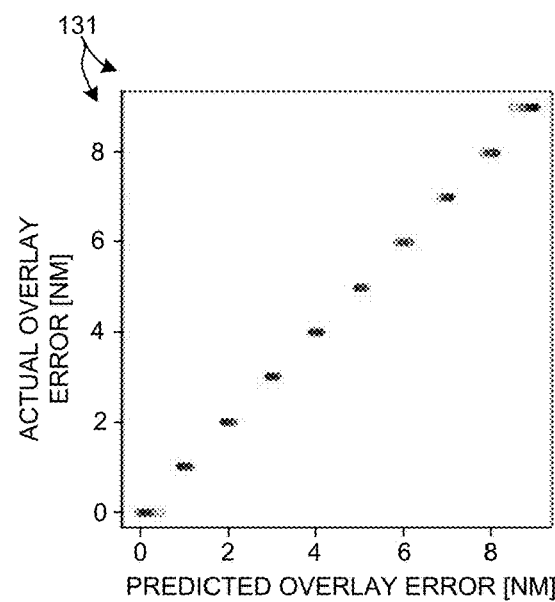
FIG. 10 depicts a plot 131 of simulation results indicative of actual overlay error on the y-axis and corresponding predicted overlay error on the x-axis for the simulation as described with reference to FIG. 9.

FIG. 10 depicts a plot 131 of simulation results indicative of actual overlay error on the y-axis (i.e., known overlay error values) and corresponding predicted overlay error on the x-axis (i.e., as measured by a trained image-based measurement model) for the simulation as described with reference to FIG. 9. The results depicted in plot 131 include measurements of images that participated in the training set and images that did not participate in the training set. As depicted in FIG. 10, the simulated measurement results are tightly grouped with the corresponding, known values.

Figure 11:
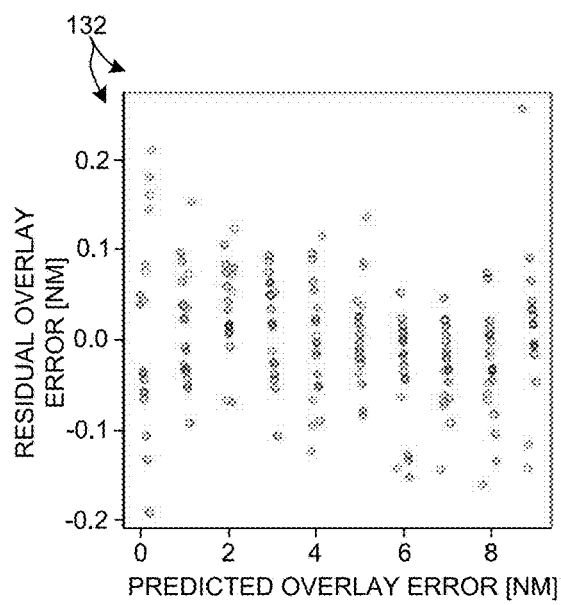
FIG. 11 depicts a plot 132 indicative of the residual overlay error values associated with each measurement point depicted in FIG. 10.

FIG. 11 depicts a plot 132 indicative of the residual overlay error values associated with each measurement point depicted in FIG. 10.

Figure 12:
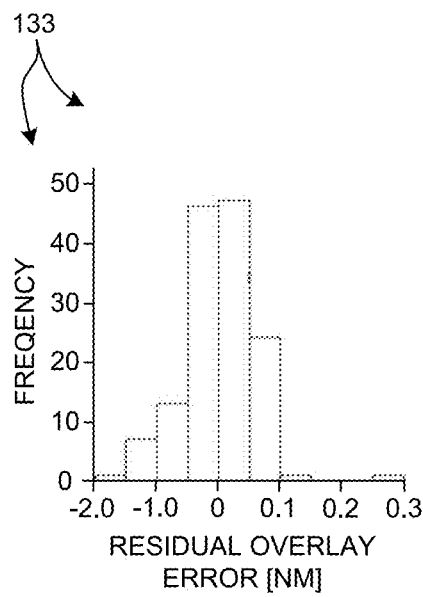
FIG. 12 depicts a plot 133 illustrating the distribution of the residual values depicted in FIG. 11 for measurement points associated with training images.

FIG. 12 depicts a plot 133 illustrating the distribution of the residual values depicted in FIG. 11 for the measurement points associated with training images. The sigma value of the residual value for this set of images is 0.06 nanometers.

Figure 13:
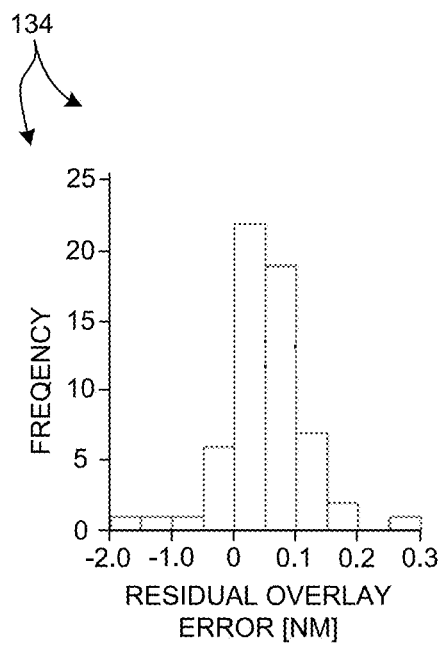
FIG. 13 depicts a plot 134 illustrating the distribution of the residual values depicted in FIG. 10 for measurement points associated with images that did not participate in the training data set.

FIG. 13 depicts a plot 134 illustrating the distribution of the residual values depicted in FIG. 10 for the measurement points associated with images that did not participate in the training data set. The sigma value of the residual value for this set of images is 0.14 nanometers.

As described hereinbefore, the measurement methods and systems described herein are not constrained to specialized targets. In general, any target that exhibits sensitivity to a parameter of interest when imaged by the available imaging system may be employed in accordance with the methods and systems described herein.

However, in some examples, it is advantageous to employ specialized measurement targets that exhibit high sensitivity to a parameter of interest when imaged by the available imaging system to enhance image-based measurement performance. For example, when signal response metrology is applied to the measurement of overlay error as described herein, it is desirable to maximize the number of pixels that change due to changes in overlay error in the x and y directions.

Figure 14A:
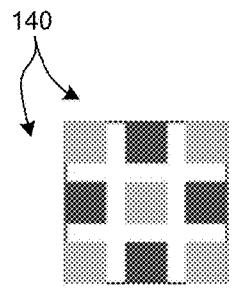
FIGS. 14A-14D exhibit metrology targets 140-143, respectively, that may be advantageous for image-based measurement of overlay errors in some embodiments.
Figure 14B:
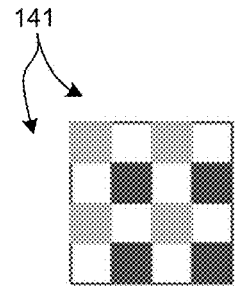
Figure 14C:
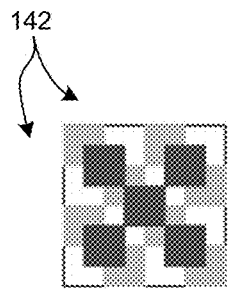
Figure 14D:
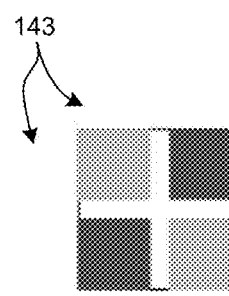

FIGS. 14A-14D exhibit metrology targets 140-143, respectively, that may be advantageous for image-based measurement of overlay errors. In some embodiments, the metrology targets depicted in FIGS. 14A-14D are one micron by one micron. In some other embodiments, the metrology targets depicted in FIGS. 14A-14D are three microns by three microns. In general, the metrology targets depicted in FIGS. 14A-14D may be any suitable dimension. In examples depicted in FIGS. 14A-14D, the dark shaded areas are printed on one layer of semiconductor wafer and the light shaded areas are printed on another layer of the semiconductor layer. In some embodiments, the light and dark shaded areas are solid blocks. However, in some other embodiments, the light and dark shaded areas are grating structures. When there is overlap between the grating structures, the grating structures will interact. The resulting changes in intensity provide additional and different signals compared to embodiments where the light and dark shaded areas are solid blocks. FIG. 14A depicts a metrology target 140 with space between each element. In this manner, a certain amount of overlay error may occur without any of the elements on one layer overlapping with any other elements on the other layer. In this manner, the overlay error is determined primarily by changes in pixels located between the elements. FIG. 14B depicts a metrology target 141 with elements of each layer arranged such that any overlay error in both the x and y directions results in an overlap between elements on one layer and elements on the other layer. FIG. 14C depicts a metrology target 142 having elements of each layer arranged such that any overlay error in any directions results in changes in the overlap between elements on one layer and elements on the other layer. FIG. 14D depicts a metrology target 143 that is similar to metrology target 140 depicted in FIG. 14A, except that there are fewer, larger elements printed on each layer. This may be advantageous when the resolution of the metrology system is not sufficient to clearly resolve the smaller elements depicted in FIGS. 14A-14C.

Figure 15A:
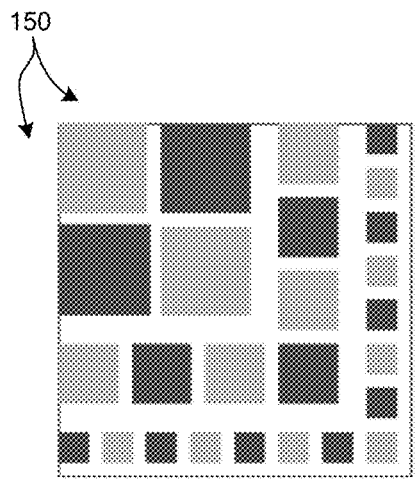
FIGS. 15A-15B exhibit metrology targets 150-151, respectively, that may be advantageous for image-based measurement of overlay errors in some embodiments.
Figure 15B:
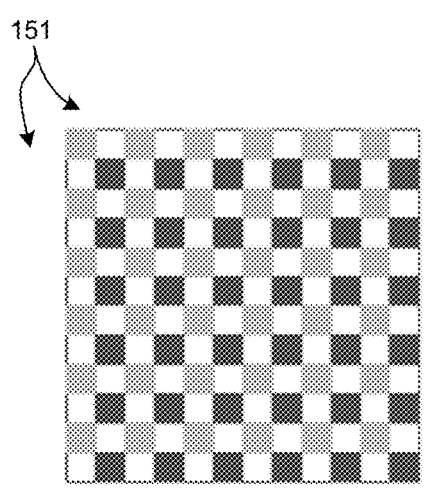

FIGS. 15A-15B exhibit metrology targets 150-151, respectively, that may be advantageous for image-based measurement of overlay errors. In some embodiments, the metrology targets depicted in FIGS. 15A-15B are three microns by three microns. In some other embodiments, the metrology targets depicted in FIGS. 15A-15B are five microns by five microns. In general, the metrology targets depicted in FIGS. 15A-15B may be any suitable dimension. In examples depicted in FIGS. 15A-15B, the dark shaded areas are printed on one layer of semiconductor wafer and the light shaded areas are printed on another layer of the semiconductor layer. In some embodiments, the light and dark shaded areas are solid blocks. However, in some other embodiments, the light and dark shaded areas are grating structures.

FIG. 15A depicts a metrology target 150 with space between each element. In this manner, a certain amount of overlay error may occur without any of the elements on one layer overlapping with any other elements on the other layer. In this manner, the overlay error is determined primarily by changes in pixels located between the elements. In addition, metrology target 150 includes different sized elements. Such a target may be advantageous when it is desirable to use one metrology target with various metrology systems having different imaging resolutions.

FIG. 15B depicts a metrology target 151 with elements of each layer arranged such that any overlay error in both the x and y directions results in an overlap between elements on one layer and elements on the other layer.

Figure 16A:
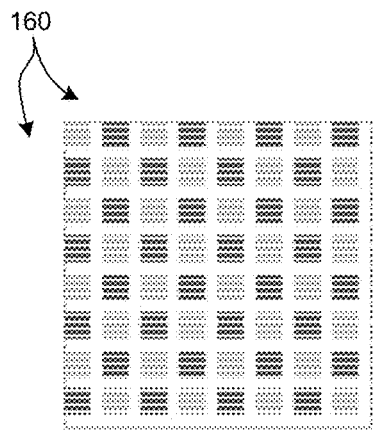
FIGS. 16A-16B exhibit metrology targets 160-161, respectively, that may be advantageous for image-based measurement of overlay errors in some embodiments.
Figure 16B:
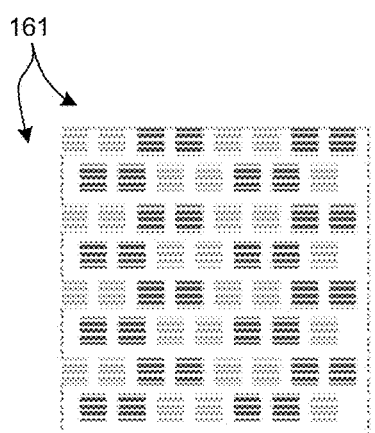

FIGS. 16A-16B exhibit metrology targets 160-161, respectively, that may be advantageous for image-based measurement of overlay errors. In some embodiments, the metrology targets depicted in FIGS. 16A-16B are seven microns by seven microns. In general, the metrology targets depicted in FIGS. 15A-15B may be any suitable dimension. In examples depicted in FIGS. 16A-16B, the dark shaded areas are printed on one layer of semiconductor wafer and the light shaded areas are printed on another layer of the semiconductor layer. In some embodiments, the light and dark shaded areas are solid blocks. However, in some other embodiments, the light and dark shaded areas are grating structures.

FIG. 16A depicts a metrology target 160 with space between each element. In this manner, a certain amount of overlay error may occur without any of the elements on one layer overlapping with any other elements on the other layer. In this manner, the overlay error is determined primarily by changes in pixels located between the elements.

FIG. 16B depicts a metrology target 161 with multiple elements of each layer disposed adjacent to one another.

Figure 17A:
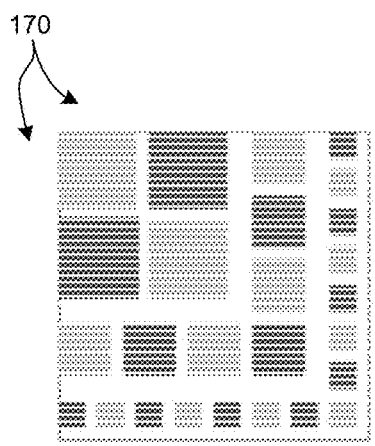
FIGS. 17A-17B exhibit metrology targets 170-171, respectively, that may be advantageous for image-based measurement of overlay errors in some embodiments.
Figure 17B:
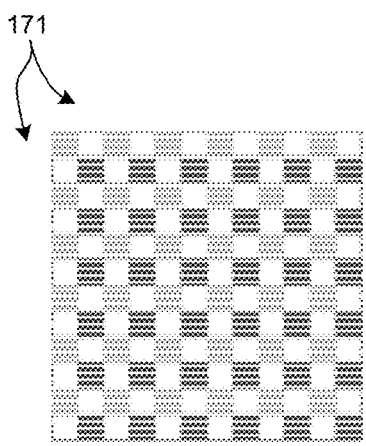

FIGS. 17A-17B exhibit metrology targets 170-171, respectively, that may be advantageous for image-based measurement of overlay errors. In some embodiments, the metrology targets depicted in FIGS. 17A-17B are ten microns by ten microns. However, in general, the metrology targets depicted in FIGS. 17A-17B may be any suitable dimension. In examples depicted in FIGS. 17A-17B, the dark shaded areas are printed on one layer of semiconductor wafer and the light shaded areas are printed on another layer of the semiconductor layer. In some embodiments, the light and dark shaded areas are solid blocks. However, in some other embodiments, the light and dark shaded areas are grating structures.

FIG. 17A depicts a metrology target 170 with space between each element. In this manner, a certain amount of overlay error may occur without any of the elements on one layer overlapping with any other elements on the other layer. In this manner, the overlay error is determined primarily by changes in pixels located between the elements. In addition, metrology target 170 includes different sized elements. Such a target may be advantageous when it is desirable to use one metrology target with various metrology systems having different imaging resolutions.

FIG. 17B depicts a metrology target 171 with elements of each layer arranged such that any overlay error in both the x and y directions results in an overlap between elements on one layer and elements on the other layer.

In another further aspect, the methods and systems described herein are not limited only to the measurement of overlay errors. In general, the aforementioned image-based measurement techniques may be applied to the measurement of other process, structure, dispersion parameters, or any combination of these parameters. By way of non-limiting example, any of critical dimension, overlay error, focus, and dose may be measured using the aforementioned techniques.

In another further aspect, the methods and systems for training the image-based measurement model include an optimization algorithm to automate any or all of the elements required to arrive at a trained image-based measurement model.

In some examples, an optimization algorithm is configured to maximize the performance of the measurement (defined by a cost function) by optimizing any or all of the following parameters: the list of image filters, the parameters of the filters, the type of feature extraction model, the parameters of the selected feature extraction model, the type of measurement model, the parameters of the selected measurement model. The optimization algorithm can include user defined heuristics and can be combination of nested optimizations (e.g., combinatorial and continuous optimization).

In a further aspect, image data from different targets is collected for model building, training, and measurement. The use of image data associated with multiple targets having different structure, but formed by the same process conditions increases the information embedded in the model and reduces the overlay correlation to process or other parameter variations. In particular, the use of training data that includes images of multiple, different targets at one or more measurement sites enables more accurate estimation of values of parameters of interest.

In another further aspect, signals from multiple targets can be processed to reduce sensitivity to process variations and increase sensitivity to the parameters of interest. In some examples, signals from images, or portions of images, of different targets are subtracted from one another. In some other examples, signals from images, or portions of images, of different targets are fit to a model, and the residuals are used to build, train, and use the image-based measurement model as described herein. In one example, image signals from two different targets are subtracted to eliminate, or significantly reduce, the effect of process noise in each measurement result. In general, various mathematical operations can be applied between the signals from different target images, or portions of target images to determine image signals with reduced sensitivity to process variations and increased sensitivity to the parameters of interest.

In another further aspect, measurement data derived from measurements performed by a combination of multiple, different measurement techniques is collected for model building, training, and measurement. The use of measurement data associated with multiple, different measurement techniques increases the information content in the combined set of signals and reduces the overlay correlation to process or other parameters variations. Measurement data may be derived from measurements performed by any combination of multiple, different measurement techniques. In this manner, different measurement sites may be measured by multiple, different measurement techniques (e.g., CD-SEM, imaging techniques such as 2-D BPR, scatterometry, etc.) to enhance the measurement information available for estimation of parameters of interest.

In general, any measurement technique, or combination of two or more measurement techniques may be contemplated within the scope of this patent document as the data processed by the feature extraction model and the image-based measurement model for training and measurement is in vector form. Because the signal response metrology techniques as described herein operate on vectors of data, each pixel of image data is treated independently. In addition, it is possible to concatenate data from multiple, different metrologies, regardless of whether the data is two dimensional image data, one dimensional image data, or even single point data.

Exemplary measurement techniques that may provide data for analysis in accordance with the signal response metrology techniques described herein include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WAXS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), x-ray tomography, and x-ray ellipsometry. In general, any metrology technique applicable to the characterization of semiconductor structures, including image based metrology techniques, may be contemplated, individually, or in any combination.

In another further aspect, signals measured by multiple metrologies can be processed to reduce sensitivity to process variations and increase sensitivity to the parameters of interest. In some examples, signals from images, or portions of images, of targets measured by different metrologies are subtracted from one another. In some other examples, signals from images, or portions of images, of targets measured by different metrologies are fit to a model, and the residuals are used to build, train, and use the image-based measurement model as described herein. In one example, image signals from a target measured by two different metrologies are subtracted to eliminate, or significantly reduce, the effect of process noise in each measurement result. In general, various mathematical operations can be applied between the signals of target images, or portions of target images, measured by different metrologies to determine image signals with reduced sensitivity to process variations and increased sensitivity to the parameters of interest.

In general, image signals from multiple targets each measured by multiple metrology techniques increases the information content in the combined set of signals and reduces the overlay correlation to process or other parameters variations.

FIG. 19 illustrates a system 300 for measuring characteristics of a specimen in accordance with the exemplary methods presented herein. As shown in FIG. 19, the system 300 may be used to perform spectroscopic ellipsometry measurements of one or more structures of a specimen 301. In this aspect, the system 300 may include a spectroscopic ellipsometer equipped with an illuminator 302 and a spectrometer 304. The illuminator 302 of the system 300 is configured to generate and direct illumination of a selected wavelength range (e.g., 150-850 nm) to the structure disposed on the surface of the specimen 301. In turn, the spectrometer 304 is configured to receive illumination reflected from the surface of the specimen 301. It is further noted that the light emerging from the illuminator 302 is polarized using a polarization state generator 307 to produce a polarized illumination beam 306. The radiation reflected by the structure disposed on the specimen 301 is passed through a polarization state analyzer 309 and to the spectrometer 304. The radiation received by the spectrometer 304 in the collection beam 308 is analyzed with regard to polarization state, allowing for spectral analysis by the spectrometer of radiation passed by the analyzer. These spectra 311 are passed to the computing system 330 for analysis of the structure.

As depicted in FIG. 19, system 300 includes a single measurement technology (i.e., SE). However, in general, system 300 may include any number of different measurement technologies. By way of non-limiting example, system 300 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 300 may include one or more computing systems 330 employed to perform overlay measurements based on image-based measurement models developed in accordance with the methods described herein.

The one or more computing systems 330 may be communicatively coupled to the spectrometer 304. In one aspect, the one or more computing systems 330 are configured to receive measurement data 311 associated with measurements of the structure of specimen 301.

It should be recognized that the various steps described throughout the present disclosure may be carried out by a single computer system 330 or, alternatively, a multiple computer system 330. Moreover, different subsystems of the system 300, such as the spectroscopic ellipsometer 304, may include a computer system suitable for carrying out at least a portion of the steps described herein. Therefore, the aforementioned description should not be interpreted as a limitation on the present invention but merely an illustration. Further, the one or more computing systems 330 may be configured to perform any other step(s) of any of the method embodiments described herein.

In addition, the computer system 330 may be communicatively coupled to the spectrometer 304 in any manner known in the art. For example, the one or more computing systems 330 may be coupled to computing systems associated with the spectrometer 304. In another example, the spectrometer 304 may be controlled directly by a single computer system coupled to computer system 330.

The computer system 330 of the metrology system 300 may be configured to receive and/or acquire data or information from the subsystems of the system (e.g., spectrometer 304 and the like) by a transmission medium that may include wireline and/or wireless portions. In this manner, the transmission medium may serve as a data link between the computer system 330 and other subsystems of the system 300.

Computer system 330 of the integrated metrology system 300 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 330 and other systems (e.g., memory on-board metrology system 300, external memory, reference measurement source 320, or other external systems). For example, the computing system 330 may be configured to receive measurement data from a storage medium (i.e., memory 332 or an external memory) via a data link. For instance, spectral results obtained using spectrometer 304 may be stored in a permanent or semi-permanent memory device (e.g., memory 332 or an external memory). In this regard, the spectral results may be imported from on-board memory or from an external memory system. Moreover, the computer system 330 may send data to other systems via a transmission medium. For instance, an integrated measurement model or a specimen parameter 340 determined by computer system 330 may be communicated and stored in an external memory. In this regard, measurement results may be exported to another system.

Computing system 330 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 334 implementing methods such as those described herein may be transmitted over a transmission medium such as a wire, cable, or wireless transmission link. For example, as illustrated in FIG. 19, program instructions 334 stored in memory 332 are transmitted to processor 331 over bus 333. Program instructions 334 are stored in a computer readable medium (e.g., memory 332). Exemplary computer-readable media include read-only memory, a random access memory, a magnetic or optical disk, or a magnetic tape.

In some examples, the model building, training, and measurement methods described herein are implemented as an element of a SpectraShape® optical critical-dimension metrology system available from KLA-Tencor Corporation, Milpitas, Calif., USA. In this manner, the model is created and ready for use immediately after the DOE wafer spectra are collected by the system.

In some other examples, the model building and training methods described herein are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

Although several examples are described hereinbefore with reference to an image-based overlay measurement model, the methods and systems described herein may involve other process models (e.g., focus, dose, etch or deposition processing). The methods and systems described herein may also involve other metrology technologies (e.g. SEM, TEM, AFM, X-ray). Moreover, the methods and systems described herein are discussed with reference to imaging metrology systems, but can be also applied to other metrologies (e.g., spectroscopic ellipsometers, reflectometers, BPR systems, CD-SAXS, XRR, etc.).

In yet another aspect, the image-based measurement model results described herein can be used to provide active feedback to a process tool (e.g., lithography tool, etch tool, deposition tool, etc.). For example, values of overlay error determined using the methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively.

In general, the systems and methods described herein can be implemented as part of the process of preparing a measurement model for off-line or on-tool measurement. In addition, both measurement models and any reparameterized measurement model may describe one or more target structures and measurement sites.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A method comprising:
   receiving a first amount of image data associated with images of a first plurality of sites on a surface of a semiconductor wafer with known values of at least one parameter of interest, wherein the first amount of image data is derived from measurements performed by at least one metrology technique;
   determining a feature extraction model based on at least a portion of each of the plurality of images of the first amount of image data, wherein the feature extraction model reduces a dimension of the first amount of image data to generate a reduced amount of image data; and
   training an image based measurement model based on the reduced amount of image data as input to the image based measurement model and the known values of the at least one parameter of interest as output training data.

2. The method of claim 1, wherein the images are overlay images and the parameter of interest is overlay error.

3. The method of claim 1, wherein each of the known values of at least one parameter of interest is any of a process parameter value, a structural parameter value, a dispersion parameter value, and a layout parameter value.

4. The method of claim 1, wherein the images of the first plurality of sites are each captured from different locations on a design of experiments wafer.

5. The method of claim 1, further comprising:
   filtering each of the images of the first plurality of sites.

6. The method of claim 1, wherein the feature extraction model is any of a principal component analysis (PCA) model, an independent component analysis (ICA) model, a kernel PCA model, a non-linear PCA model, a fast Fourier transform (FFT) model, a discrete cosine transform (DCT) model, and a wavelet model.

7. The method of claim 1, wherein the image based measurement model is any of a linear model, a polynomial model, a neural network model, a support vector machines model, a decision tree model, and a random forest model.

8. The method of claim 1, wherein the first amount of image data includes a combination of images of a plurality of different metrology targets formed by the same process conditions.

9. The method of claim 1, wherein the first amount of image data image includes an image or combination of images acquired by a plurality of different metrology techniques.

10. The method of claim 1, wherein the first amount of image data includes image signals associated with more than one target feature at any of the first plurality of sites.

11. The method of claim 1, wherein the first amount of image data includes image signals associated with measurements by more than one metrology technique.

12. The method of claim 1, wherein the determining the feature extraction model involves determining a difference between image signals from images of different targets, image signals from images acquired by different metrology techniques, or a combination of both.

13. The method of claim 1, wherein the determining the feature extraction model involves determining residuals of a model fit to image signals from images of different targets, image signals from images acquired by different metrology techniques, or a combination of both.

14. The method of claim 1, wherein the metrology target is an on-device structure.

15. The method of claim 1, further comprising:
   receiving a second amount of image data associated with images of a second plurality of metrology targets, wherein the second amount of image data is derived from measurements performed by the same at least one metrology technique;
   determining values of at least one parameter of interest associated with each of the second plurality of metrology targets based on a fitting of the second amount of image data to the trained image based measurement model; and
   storing the values of the at least one parameter of interest in a memory.

16. A system comprising:
   a metrology tool including an illumination source and a detector configured to perform measurements of a target structure; and
   a computing system configured to:
      receive a first amount of image data associated with images of a first plurality of sites on a surface of a semiconductor wafer with known values of at least one parameter of interest, wherein the first amount of image data is derived from measurements performed by at least one metrology technique;
      determine a feature extraction model based on at least a portion of each of the plurality of images of the first amount of image data, wherein the feature extraction model reduces a dimension of the first amount of image data to generate a reduced amount of image data; and
      train an image based measurement model based on the reduced amount of image data as input to the image based measurement model and the known values of the at least one parameter of interest as output training data.

17. The system of claim 16, wherein the computing system is further configured to:
   receive a second amount of image data associated with images of a second plurality of metrology targets, wherein the second amount of image data is derived from measurements performed by the same at least one metrology technique;
   determine values of at least one parameter of interest associated with each of the second plurality of metrology targets based on a fitting of the second amount of image data to the trained image based measurement model; and
   store the values of the at least one parameter of interest in a memory.

18. The system of claim 16, wherein the computing system is further configured to:
filter each of the images of the first plurality of sites.

19. The system of claim 16, wherein the first amount of image data includes a combination of images of a plurality of different metrology targets formed by the same process conditions.

20. The system of claim 16, wherein the first amount of image data image includes an image or combination of images acquired by a plurality of different metrology techniques.

21. The system of claim 16, wherein the determining the feature extraction model involves determining a difference between image signals from images of different targets, image signals from images acquired by different metrology techniques, or a combination of both.

22. The system of claim 16, wherein the determining the feature extraction model involves determining residuals of a model fit to image signals from images of different targets, image signals from images acquired by different metrology techniques, or a combination of both.

23. The system of claim 16, wherein the metrology target is an on-device structure.

24. A method comprising:
providing illumination light to a plurality of measurement sites on a surface of a semiconductor wafer from an illumination source of a metrology system;
detecting an amount of light from each of the plurality of measurement sites in response to the illumination light by a detector of the metrology system;
generating a plurality of images of the plurality of measurement sites based on the detected amounts of light, the plurality of images comprising an amount of image data;
determining image features from at least a portion of the amount of image data based on an application of a trained feature extraction model;
determining a value of at least one parameter of interest associated with each of the plurality of sites based on a fitting of the determined image features to a trained image-based measurement model;
storing the at least one parameter value in a memory; wherein further comprising:
generating the trained image-based measurement model, wherein the generating involves;
receiving a first amount of image data associated with images of a first plurality of sites on a surface of a semiconductor wafer with known values of at least one parameter of interest, wherein the first amount of image data is derived from measurements performed by at least one metrology technique;
determining a feature extraction model based on at least a portion of each of the plurality of images of the first amount of image data, wherein the feature extraction model reduces a dimension of the first amount of image data; and
training an image based measurement model based on features extracted from the plurality of images and the known values of the at least one parameter of interest.

* * * * *